United States Patent [19]
Cavazza

[11] Patent Number: 6,013,670
[45] Date of Patent: Jan. 11, 2000

[54] USE OF ALKANOYL L-CARNITINES FOR THE THERAPEUTICAL TREATMENT OF CHRONIC INFLAMMATORY BOWEL DISEASES

[75] Inventor: Claudio Cavazza, Rome, Italy

[73] Assignee: Sigma-Tau Industrie Farmaceutiche Riunite S.p.A., Italy

[21] Appl. No.: 08/868,627

[22] Filed: Jun. 4, 1997

[30] Foreign Application Priority Data

Jun. 6, 1996 [IT] Italy .................. RM96A0396

[51] Int. Cl.⁷ .................. A61K 31/205; A61K 31/22
[52] U.S. Cl. .................. 514/547; 514/556
[58] Field of Search .................. 514/547, 556

[56] References Cited

FOREIGN PATENT DOCUMENTS 559625  9/1993  European Pat. Off. .

OTHER PUBLICATIONS

Morrison & Boyd, Organic Chemistry, fifth edition, pp. 858–859, 1990.

*Primary Examiner*—Phyllis G. Spivack
*Attorney, Agent, or Firm*—Nixon & Vanderhye

[57] ABSTRACT

The present invention relates to a therapeutic use of the lower alkanoyl L-carnitines and the pharmacologically acceptable salts thereof in pharmaceutical compositions for the treatment of ulcerative colitis.

9 Claims, No Drawings

USE OF ALKANOYL L-CARNITINES FOR THE THERAPEUTICAL TREATMENT OF CHRONIC INFLAMMATORY BOWEL DISEASES

The present invention relates to a new therapeutic use of the lower alkanoyl L-carnitines and their pharmacologically acceptable salts to produce pharmaceutical compositions for the treatment of chronic inflammatory bowel diseases, and, in particular, ulcerative colitis.

The present invention also relates to pharmaceutical compositions suitable for rectal administration, particularly in the form of foams or enemas, containing the above-mentioned alkanoyl L-carnitines.

Ulcerative colitis is an inflammatory, ulcerative disease of the colon of unknown etiology, very often characterized by hematic diarrhea.

It usually originates in the recto-sigmoid area, from which it may spread proximally with possible involvement of the entire colon. Alternatively, it may attack a substantial portion of the large bowel right from the outset.

The complications of ulcerative colitis are particularly severe: it has been documented, in fact, that there is an enormous increase in the risk of colon cancer in patients suffering from ulcerative colitis. The incidence of colon cancer increases with both involvement of the entire colon and with a duration of disease exceeding 10 years.

In both the mild-to-moderate forms and the moderately or distinctly severe forms of the disease, corticosteroids constitute the drugs of choice, namely hydrocortisone, betamethasone and prednisone.

In the mild-to-moderate forms, physiological solution containing hydrocortisone is administered via an enema which is retained in the bowel as long as possible.

In the moderately severe forms, systemic corticosteroid therapy is necessary, consisting generally in 10–15 mg of prednisone t.i.d. or q.i.d. per os, which is capable of inducing drastic remission.

In the more severe forms requiring admission to hospital, the corticosteroid therapy is administered parenterally.

Both the systemic and topical administration of these drugs gives rise to serious side effects, mainly related to interference with the hypothalamo-pituitary-adrenal axis.

The side effects due to topical treatment of ulcerative colitis with these traditional corticosteroids are, for instance, transient or prolonged depression of adrenocortical function, weight gain, acne and moon face.

Though it is well known, particularly in the moderately severe forms of the disease, that the daily corticosteroid dose can be gradually reduced to 10–20 mg per week after 1–2 weeks of treatment, even such low corticosteroid doses continue to induce harmful side effects, the elimination or at least the drastic reduction of which constitutes a therapeutic goal of primary importance.

The object of the present invention is to provide pharmaceutical compositions for the treatment of chronic inflammatory bowel diseases, particularly ulcerative colitis, which, while affording equivalent therapeutic benefit, make it possible to use a lower daily dose of corticosteroid drug, with a consequent distinct reduction in the side effects induced by such drugs.

A further object of the present invention is to provide a composition of the above-mentioned type which enables complete remission of symptoms to be achieved and which lends itself to rectal administration, in the form of a foam or enema, thus making it possible to avoid corticosteroid administration via the parenteral route even in the most severe cases.

These objects are achieved according to the present invention by means of the use of lower alkanoyl L-carnitines in which the alkanoyl group, straight or branched, has 2–6 carbon atoms and of their pharmacologically acceptable salts to produce the aforementioned compositions. The preferred alkanoyl L-carnitines are acetyl, propionyl, butyryl, isobutyryl, valeryl and isovaleryl L-carnitine. Propionyl L-carnitine, butyryl L-carnitine and their pharmacologically acceptable salts are particularly preferred.

What is meant by a pharmacologically acceptable salt of an alkanoyl L-carnitine is any salt of the latter with an acid which does not give rise to unwanted toxic or side effects. These acids are well known to pharmacologists and pharmacy experts.

Non-limiting examples of such salts are, for instance, chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

Though, according to the present invention, the alkanoyl L-carnitine and the reduced dose of corticosteroid can be administered orally, the preferred alkanoyl L-carnitine administration route is rectal. In particular, those forms of rectal administration, such as foams and enemas, are preferred, which allow prolonged contact between the alkanoyl L-carnitine and the intestinal tract affected by the inflammatory ulcerative disease.

The preparation of these foams and enemas and the choice of appropriate vehicles and excipients are well known to pharmacy experts.

These compositions capable of being administered by the rectal route may contain additional active ingredients such as antidiarrhoea agents, antibiotics, anaesthetics, stool softeners and lubricants.

For example, an enema composition comprises from approximately 3 to approximately 15 grams, preferably 6–12 grams, of alkanoyl L-carnitine and possibly 400–600 mg of hydrocortisone or 20–50 mg of prednisone per liter of physiological solution.

Though the daily dose will depend, according to the judgement of the primary care physician, on the subject's weight, age and general condition, it is generally advisable to administer 14 g/day—preferably 2–3 g/day—of alkanoyl L-carnitine or a stoichiometrically equivalent amount of one of its pharmacologically acceptable salts. In the preferred rectal administration form, an enema of 500-mL physiological solution containing 5–10 g of alkanoyl L-carnitine—e.g. 6 g of propionyl L-carnitine—is administered twice daily.

Larger doses can safely be administered in view of the substantial non-toxicity of the alkanoyl L-carnitines.

Details are given here below of a clinical study demonstrating the activity of the compounds according to the invention.

Three male patients suffering from ulcerative rectocolitis diagnosed by endoscopy and histological examination of biopsy samples, with a BMI (Body Mass Index) of 25 $kg/m^2$ and a DCAI (Crohn's Disease Activity Index) of approximately 180 (Gastroenterology 70: 439–444, 1976; Vol. 70, no. 3), on treatment with steroids (prednisone 0.20 mg/kg/day) were treated twice daily for 2 months with an enema containing 6 g of propionyl L-carnitine dissolved in 500 mL of physiological solution.

After only one week's treatment an improvement in the clinical picture was already noticeable with a reduction in the number of daily bowel movements and an improvement in the consistency of the faeces, as well as reduced losses of blood and mucus.

Later in the course of therapy, the subjective symptoms and the objective clinical findings continued to improve with reduction of the CDAI to approximately 120 by the end of the second month.

Thanks to this improvement the patients were able to reduce their cortisone therapy to approximately 0.8 mg/kg/day.

The endoscopic investigation showed a distinct improvement of the ulcerative lesions with areas of re-epithelialisation and non-friable mucosa on contact with the instrument.

The histological examination revealed a distinct reduction of the inflammation.

No side effects were observed, and patient compliance was optimal.

The results obtained show that by the end of the course of treatment the use of propionyl L-carnitine had significantly reduced (by about 40%) the amount of steroid drug administered to the patients, thus leading to a substantial reduction in its side effects.

I claim:

1. A method of treating chronic inflammatory bowel disease comprising administration of an alkanoyl L-carnitine wherein the alkanoyl group is straight or branched and has 2–6 carbon atoms or the pharmacologically acceptable salts thereof.

2. A method of claim 1 wherein said chronic inflammatory bowel disease is ulcerative colitis.

3. A method of claim 1 wherein said alkanoyl L-carnitine is selected from the group consisting of acetyl, propionyl, butyryl, isobutyryl, valeryl and isovaleryl L-carnitine.

4. A method of claim 1 wherein administration is selected from the group consisting of oral, parenteral, and a rectal route.

5. A method of claim 4 wherein said route is rectal and said composition is a foam or enema.

6. A method of claim 5 wherein the foam or enema further comprises an amount of a corticosteroid having an anti-inflammatory action.

7. A method of claim 6 wherein said corticosteroid is selected from the group consisting of hydrocortisone, betamethasone, and prednisone.

8. A method of claim 5 wherein said foam or enema further comprises a compound selected from the group consisting of an antidiarrhea agent, antibiotic, anesthetic, stool softener, and a lubricant.

9. A method of claim 1, 2, 3, 4, 5, 6, 7 or 8 wherein said pharmacologically acceptable salt of alkanoyl L-carnitine is selected from the group consisting of chloride, bromide, orotate, acid aspartate, acid citrate, acid phosphate, fumarate, acid fumarate, lactate, maleate, acid maleate, acid oxalate, acid sulphate, glucose phosphate, tartrate, and acid tartrate.

* * * * *